(12) United States Patent
Bakker et al.

(10) Patent No.: US 9,283,038 B2
(45) Date of Patent: Mar. 15, 2016

(54) HAIR REMOVING SYSTEM

(75) Inventors: Bernardus Leonardus Gerardus Bakker, Nijmegen (NL); Robbert Adrianus Maria Van Hal, Eindhoven (NL); Rieko Verhagen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2152 days.

(21) Appl. No.: 11/996,318

(22) PCT Filed: Jul. 21, 2006

(86) PCT No.: PCT/IB2006/052500
§ 371 (c)(1),
(2), (4) Date: Jan. 21, 2008

(87) PCT Pub. No.: WO2007/013008
PCT Pub. Date: Feb. 1, 2007

(65) Prior Publication Data
US 2008/0215038 A1    Sep. 4, 2008

(30) Foreign Application Priority Data
Jul. 26, 2005 (EP) .................................... 05106845

(51) Int. Cl.
*A61B 18/20* (2006.01)
*A61B 18/00* (2006.01)

(52) U.S. Cl.
CPC .............. *A61B 18/203* (2013.01); *A61B 18/20* (2013.01); *A61B 2018/00452* (2013.01); *A61B 2018/00476* (2013.01); *A61B 2018/00904* (2013.01)

(58) Field of Classification Search
CPC ............... A61B 18/20; A61B 2018/20; A61B 2018/004
See application file for complete search history.

(56) References Cited

U.S. PATENT DOCUMENTS

| 6,149,645 A * | 11/2000 | Tobinick ........................... 606/9 |
| 6,267,771 B1 | 7/2001 | Tankovich |
| 7,108,690 B1 * | 9/2006 | Lefki et al. ..................... 606/10 |
| 2001/0053907 A1 * | 12/2001 | Ota ................................. 606/10 |
| 2003/0036751 A1 | 2/2003 | Anderson |

FOREIGN PATENT DOCUMENTS

| EP | 1163887 | 12/2001 |
| JP | 6223277 A | 8/1994 |
| JP | 8050696 A | 2/1996 |
| JP | 2000245745 A | 9/2000 |
| WO | 0062700 | 10/2000 |
| WO | 02073246 | 9/2002 |
| WO | 2004083944 | 9/2004 |
| WO | 2005011510 | 2/2005 |

* cited by examiner

*Primary Examiner* — Lynsey Crandall (57) ABSTRACT

The invention relates to a system and method for removing hair. The system comprises a hair detection device and a hair-removing device (20). Since 3D information on hairs (32) is required, but due to the very dispersed presence of, e.g., human hairs (32) on skin (30), known detection devices are too slow, the invention provides a combination of two image sensors. A first image sensor (12) produces a first image, based on which a selected part is imaged with a second image sensor (14) that provides the required 3D position information with which the hair-removing device (20) can remove the hair. Thus, optimum use may be made of both fast but less accurate image sensors, such as (2D) CCDs or CMOS sensors, and accurate but slow sensors such as 3D scanning sensors.

15 Claims, 6 Drawing Sheets

HAIR REMOVING SYSTEM

The invention relates to a hair-removing system, in particular a hair-removing system comprising a hair-detection device and a hair-removing device that is operatively coupled to the hair detection device, wherein the hair detection device comprises an imaging device comprising a first image sensor, that is constructed and arranged to detect an image of a part of a skin to be treated, and a control unit that is constructed and arranged to discern in the image a hair on the part of the skin, and that is operatively coupled to the hair-removing device to control operation thereof.

WO0/62700 also relates to a hair-removing device and discloses a device with a laser source, an adjustable beam manipulator, an image sensor, and a control unit that determines a position and orientation of hair on the skin. The image sensor comprises a CCD or a CMOS sensor.

A problem of the known device relates to determining the position and/or orientation of the hair and the speed with which this is done. In order to correctly remove the hair, its position in three dimensions must be known, since otherwise the laser beam might, e.g., pass the hair without actually hitting it, et cetera. This problem also relates to other devices and methods of removing hairs that directly act on the hairs, such as electrical epilation and the like.

Known image sensors either have the problem of a very small resolution in at least one direction (usually the direction perpendicular to the skin), such as CCD or CMOS sensors, or, when they have a sufficient range and resolution in that direction, they have a very low speed of determining the position, such as 3D scanning devices that work with lenses. Since human hairs are thin objects that are also thinly spread across the skin, no known sensor provides a sufficiently high speed of determining a 3D position of hair on the skin.

It is an object of the present invention to provide a hair-removing system that is capable of sufficiently quickly determining such a position, and/or orientation, of hair on the skin.

This object is achieved by a hair-removing system according to claim 1. In particular, this system is characterized in that the imaging device comprises a second image sensor that is different from the first image sensor.

The system according to the invention allows the use of the advantages of more than one sensor, in particular more than one sensor type. For example, a first image sensor may be used to determine the position, and/or orientation, of the hair roughly but quickly. A second, different, image sensor may then be used to more precisely, albeit more slowly, determine the position, and/or orientation, in particular in all three dimensions. By using the sensor results of the first sensor, it is possible to limit the time needed for the more precise but slower scanning operation by the second image sensor, provided the latter need only image a selected part of the part of the skin that is imaged by the first sensor. That selection may be carried out by the control unit, which may be provided with image processing software/hardware etc. Various embodiments of the invention will be described below.

Preferably, but not exclusively, the part of the skin, in particular human skin, such as female skin, to be treated comprises a hair or a plurality of hairs, or a male beard et cetera. However, it is also possible for the part to comprise moles, veins (couperose) et cetera, which however require a much less high resolution.

In a special embodiment, the second image sensor is able to provide a higher spatial information density than the first image sensor, in their respective image. Spatial information on hair position and/or orientation is required, and thus it may be advantageous if a first image sensor provides a "rough" estimate, to select a part for imaging by the second image sensor. The latter may then provide the information with the desired precision, for which a corresponding desired spatial information density may be required.

In a particular embodiment, the first image sensor is constructed to provide a substantially two-dimensional image. Image sensors that are able to provide such information are relatively simple and operate quickly. Often, they do not require moving mechanical parts. In particular, the first image sensor comprises a 2D optical image sensor, preferably a charge coupled device, a CMOS device or a focal plane array of photodetectors. 2D optical image sensors are relatively cheap, fast and can easily offer a suitably high resolution. A CCD, such as a CCD camera, may have a high resolution and a large surface area, cf, CCD chips for cameras having millions of pixels and a surface area of about 10 $cm^2$. CMOS devices also have advantages, like a high frame rate in the kHz range or higher. Furthermore, since CMOS devices are chip devices, they may comprise a (or the) control unit as a built-in feature, which simplifies the system as a whole.

In a special embodiment, the first image sensor is constructed to detect an image of a part of the skin of at least 2 mm×2 mm, preferably at least 1 cm×1 cm. This relates particularly to a combination of a desired resolution, imaging optics and the number of detector elements, since it is this combination that may be used to select a size of a field of view. For example, if a CCD has 200×200 detector elements or pixels, and a required resolution is 0.01 mm, then the field of view will at most be (200×0.01 mm)×(200×0.01 mm)=2×2 mm. The required imaging optics may then easily be selected by the skilled person. Larger CCDs and/or with more pixels are available, and similar considerations hold for CMOS devices.

In a hair-removing system according to the invention, at least a part of the second image sensor is movable with respect to the first image sensor. This may relate to moving the second image sensor out of the way of the first image sensor, in order to ensure that the first image sensor has a free view of the skin to be imaged. It may also relate to moving the second image sensor with respect to the system as a whole, in order to suitably position the second image sensor and its field of view with respect to the skin to be imaged. This selection of the part of the skin to be imaged reduces the time required to do so, which is one of the important advantages of this invention. Since the first image sensor will almost always be mounted fixedly in the system as a whole, this is an alternative expression for the second image sensor being movable with respect to the first image sensor. Alternatively, and in particular, it may also relate to moving a part of the second image sensor, such as a scanning mirror.

In a special embodiment, the second image sensor has, in at least one dimension, a higher resolution than a resolution of the first image sensor in that dimension. This relates in particular to systems in which the first image sensor gives a substantially two-dimensional image, and in which the second image sensor is used to obtain more precise position information on the hairs. A simple and cheap CCD sensor, or the like, may provide a rough first image, after which a selection in the image is made, which is imaged more precisely (e.g., scanned) by the second sensor. This embodiment is for example useful in a system for removing hairs by shaving at a certain fixed depth. Herein, "depth" information is relevant only in as far as the depth is fixed, and the image is precise and accurate.

In another special embodiment, the second image sensor is constructed to scan a selected part of the part of the skin to be treated, to thus provide an image thereof, in a third dimension outside the two-dimensional image of the first image sensor. The two-dimensional image extends in two directions, and the second image sensor is then used to provide additional information on, in particular, the "missing" third dimension. Note that this information is not strictly necessary, as sometimes the "depth" or other value of the missing dimension is fixed.

In a particular embodiment, the second image sensor comprises a 3D image sensor, in particular a 3D optical image sensor with an adjustable lens that preferably is movable in a direction perpendicular to the part of the skin to be treated. The 3D image sensor may relate to any type of image sensor that is able to provide a three-dimensional image. It relates in particular to a 3D optical image sensor that may comprise a scanning system and a photodetector, and/or a (separate) CCD or CMOS device. Alternatively, arrays of photodetectors, and the like, are possible. The adjustable lens is a lens that is adjustable in focus or in distance, thus enabling scanning of a volume. The scanning of a volume, or simply scanning in one direction such as a direction perpendicular to the part of the skin to be treated, is rather time-consuming, but since the volume to be scanned may be selected to be suitably small by the control unit on the basis of the image determined by the first image sensor, the total time needed may be kept within practical boundaries. This will be elucidated further in the detailed description of some embodiments. In particular, the angle is substantially a right angle, in order to simplify the 3D imaging process. Nevertheless, other directions are also possible, with a corresponding adaptation of the determination of the image in that direction.

In a special embodiment, the lens is movable in a direction that is substantially parallel to the part of the skin to be treated. This is a useful embodiment, in which the lens may be suitably positioned for scanning, and or a subsequent laser treatment of hairs, e.g. in case the latter is performed confocally. Another reason for providing such a movement of the lens is to move the lens out of the way for a subsequent new imaging step of the first image sensor. Other uses of this feature are also contemplated.

With respect to the preceding description, it is noted that it is not necessary for an optical image sensor to detect a reflected image of a beam of radiation. It is alternatively possible to use Raman or other scattering, or to use fluorescence, possibly by covering the skin and hairs with a fluorescent substance, et cetera. It is likewise possible to use non-optical image sensors, which use other techniques to provide an image in one (z-scanning), two or three dimensions.

In a special embodiment, the system according to the invention further comprises a light source. Such a light source may have various functions. E.g., the light source may emit light that is used for imaging. It is expressly noted that the term light encompasses visible light, infrared radiation and ultraviolet radiation. The sensitivity of the image sensor(s) should be chosen accordingly. Each sensor may have its own light source, but it is also possible that one light source serves more than one purpose, or is used for more than one sensor.

In a particular embodiment, the light source may comprise in particular a LED or a laser source. A LED is very compact and energy efficient, and emits radiation in a relatively small wavelength band. This allows easy filtering, or other control of radiation, where desired. Furthermore, LEDs are easily controllable, and have a very long service life. A laser source may have a very high power density, and emits substantially monochromatic radiation, which is very well controllable by means of dedicated mirrors, filters etc. Thus, lasers are also well-suited for scanning imaging purposes. Furthermore, the obtainable power density is sufficiently high to provide a hair-removing device.

In a special embodiment of the system, the laser source is an adjustable laser source. This offers the possibility of providing one and the same laser source for both scanning and cutting, or removing, hairs.

In particular, but not exclusively, the laser source is adjustable between a first power level that enables detection without substantial damage to the skin and/or hair, and a second power level that enables inflicting sufficient damage to the hair for the hair to be subsequently removed. For example, the laser is set, by the control unit, to a low power density for imaging, and to a high power density for cutting a hair. This may be achieved by means of setting a power supply level, by means of operating a separate shutter or grey filter et cetera.

In another embodiment, the system comprises beam width control means. Such beam width control means serve to spread the energy of the beam over a controllable larger or smaller surface area. This will cause the beam to have a higher or a lower intensity, respectively. By suitably setting the beam width control means, the beam may, at a first setting, have a sufficiently low intensity to allow detection without damaging the hair, or skin. In another setting, the intensity may be sufficient for cutting, or more generally damaging, the hair. Examples of such beam width control means are an adjustable focusing/defocusing system, such as a movable lens, or a movable beam attenuator in the form of a diffusor that may be brought into and out of the path of the beam, and so forth.

The present invention also relates to a method of detecting and removing a hair on skin, the method comprising providing a hair-removing system according to the present invention, detecting a substantially two-dimensional image of a part of a skin to be treated by means of the first image sensor, selecting a portion of the part of the skin, the two-dimensional image of which contains at least one hair, by means of the control unit, scanning the selected portion with the second image sensor in at least a scanning direction that makes a non-zero angle with the image, in order to obtain a position and/or orientation of the hair in three dimensions, operating the hair-removing device to remove the hair. Here, as in the rest of this application, an image is to be understood as extending in the same direction(s) as the original part that is imaged. It is expressly not any abstract data set, not having a true extension.

This method reflects a possible use of the system according to the invention, having the advantage of a two-step imaging method, before applying the hair-removing device. Since the second imaging step is relatively time-consuming, but may be limited in area or volume by first imaging with the first image sensor, the total imaging time needed is limited. Further advantages largely correspond to those already mentioned above.

These and other aspects of the invention are apparent from and will be elucidated with reference to the embodiments described hereinafter.

Figure 1:
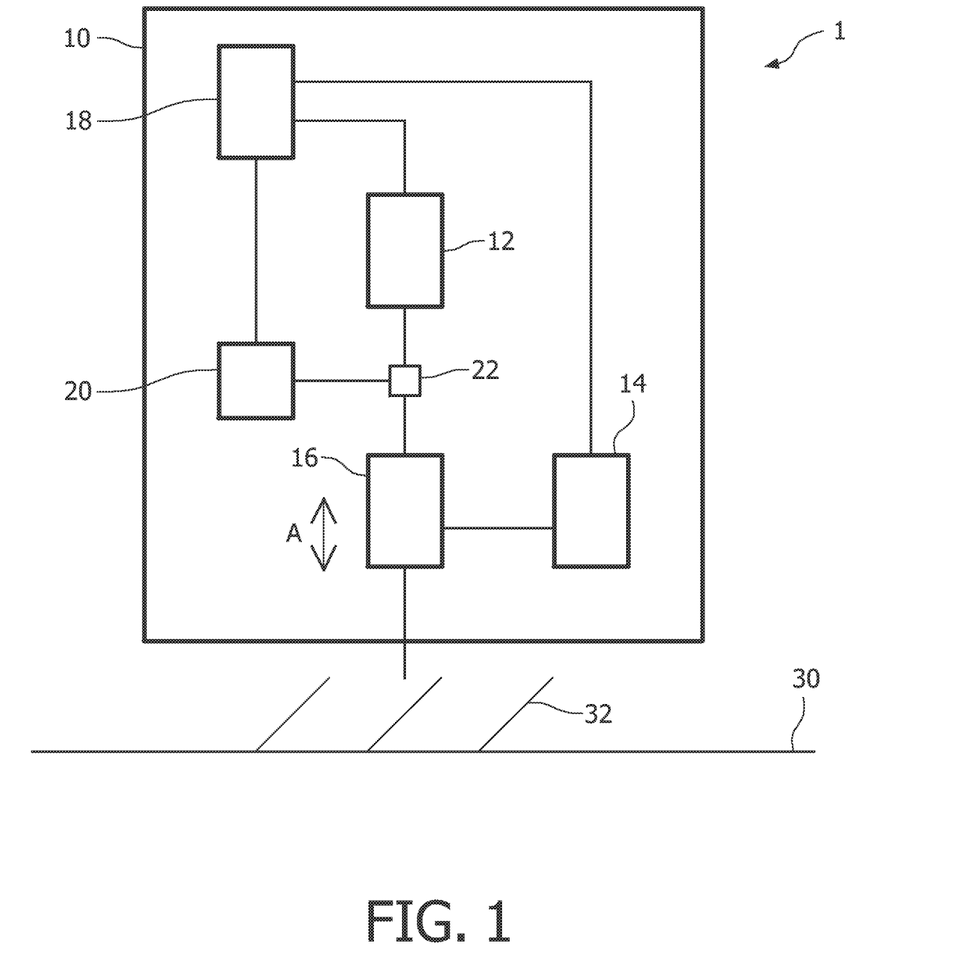
FIG. 1 diagrammatically shows a system according to the invention.

FIG. 1 very diagrammatically shows a system according to the invention. Herein, the system 1 comprises a housing 10 with a first image sensor 12, a second image sensor 14 with an adjustable lens 16, a control unit 18, a hair-removing device 20 and an optical coupling 22. In the above, the separate movable lens 16 as well as the optical coupling 22 are optional, as will be explained further on.

Also shown is a skin 30 with hairs 32 to be removed.

The housing 10 of the system 1 as shown only comprises parts that are relevant for the present invention. Obviously, additional parts, such as a power unit, an optical window etc, may be present, but are not shown.

The first image sensor 12 may comprise, e.g., a CCD camera, a CMOS device etc. The second image sensor 14 is coupled to an adjustable lens 16, and may comprise a scanning unit.

Both image sensors 12 and 14 are coupled to a control unit 18, that is constructed and arranged to discern hairs from the image as obtained by the sensors 12 and 14.

Also coupled to the control unit 18 is a hair-removing device, such as a laser system, an electrical epilating system etc. The lens 16 may be moved in the direction of arrow A, to focus at different values of z, in order to scan and produce an image in the z-dimension. Optionally, the adjustable lens 16 may be moved aside in the direction, e.g., perpendicular to arrow A in order to free a field of view of the first image sensor 12.

Figure 2:
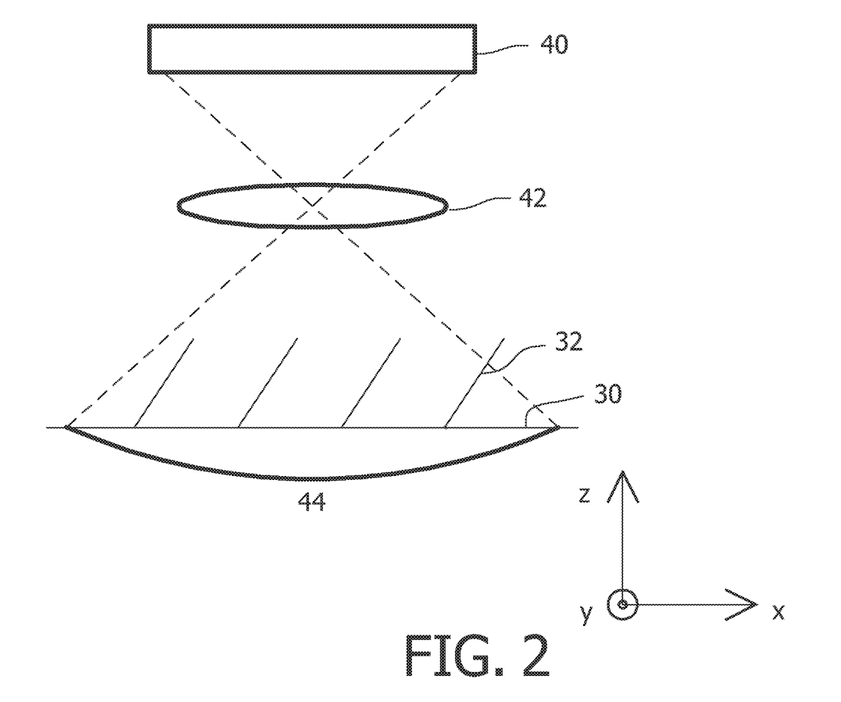
FIG. 2 diagrammatically shows a first image sensor as used in the system according to the invention.

FIG. 2 very diagrammatically shows a first image sensor as used in the system according to the invention. Herein, as in all the Figures, similar parts are denoted by the same reference numerals. In the Figure, 40 denotes a CCD, 42 denotes an optical system, while 44 denotes a field of view of the CCD.

In the Figure, more than one hair is present in the field of view of the CCD, as most CCDs have fields of view of, e.g., one or more cm$^2$. Such an area of, e.g., a human beard contains several dozens of hairs. However, the resolution, and the range in the perpendicular direction, for example the Z direction as shown in the Figure, is very limited and determined by the properties of the optical system 42. Note that a CCD can determine an image in one step, all the pixels being "filled" simultaneously.

As a CCD image sensor per se is known to the skilled person, details thereof are omitted here.

Figure 3:
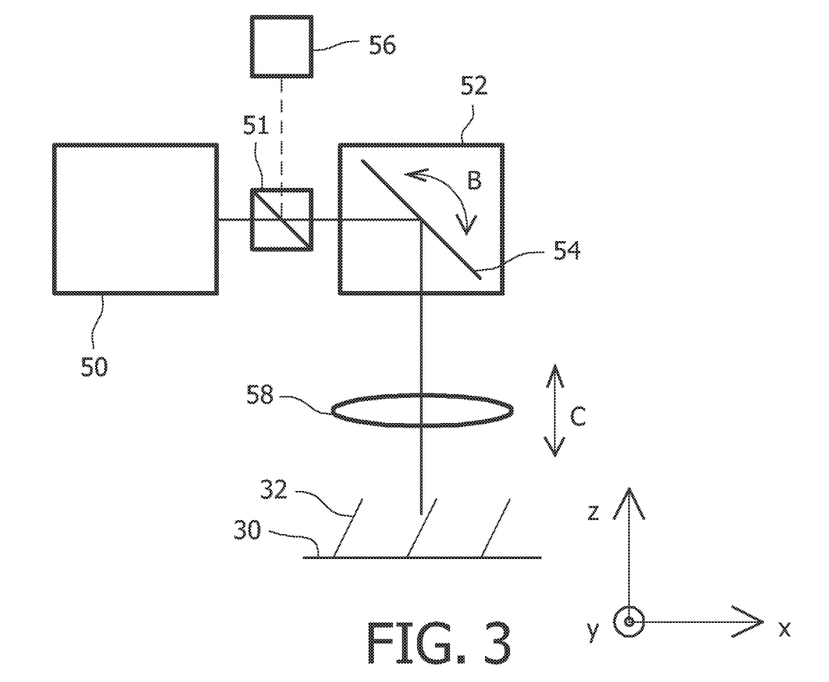
FIG. 3 diagrammatically shows a second image sensor that may be used in the system according to the invention.

FIG. 3 very diagrammatically shows a second image sensor that may be used in the system according to the invention. Herein, 50 denotes a laser source, 51 denotes a beam splitter, 52 denotes a beam manipulator with a movable mirror 54 that is movable, e.g., in the direction of arrow B. A detector is denoted by means of reference numeral 56, while a lens 58 is movable in the direction of arrow C.

Alternatively to the laser source 50, any other suitable radiation source may be selected, such as a LED with a lens. The emitted beam is partly transmitted by beam splitter 51 (which may or may not be polarizing), and partly reflected downwards, e.g., to a beam dump (not shown).

Beam manipulator 52 is, e.g., controllable by the control unit (not shown), and comprises a movable mirror 54, such as a polygon mirror or any other suitable type of scan mirror. As shown, the mirror 54 is movable, e.g. rotatable, in the direction of arrow B, in order to scan a beam of radiation across a desired area, in this case a second field of view. In practice, the field of view of the second image sensor will have dimensions of about 0.5 mm×0.5 mm in the x, y directions, and a similar dimension in the z direction. To obtain the latter range, the optical system or lens 58 is movable in the direction C. Alternatively, the optical system or lens 58 may be adjustable in optical power, i.e. the focal length thereof.

The detector 56 is optically coupled to the beam manipulator 52 via the beam splitter 51. Radiation that is reflected, Raman-scattered etc., at the skin 30 or hairs 32, is reflected by the mirror 54 towards beam splitter 51, and will be partly reflected towards detector 56.

The detector 56 may comprise a CCD or CMOS, or any other kind of photodetector or array thereof. The detector 56 will also be coupled to the control unit (not shown) in order for the control unit to determine the position and/or orientation of a hair 32 on a skin 30. For this second image sensor, a three-dimensional image will be obtained. This type of image sensor may also be referred to as a 3D scanning sensor. As it is known per se in the state of the art, further details will be omitted, but will be apparent to the skilled person.

Figure 4:
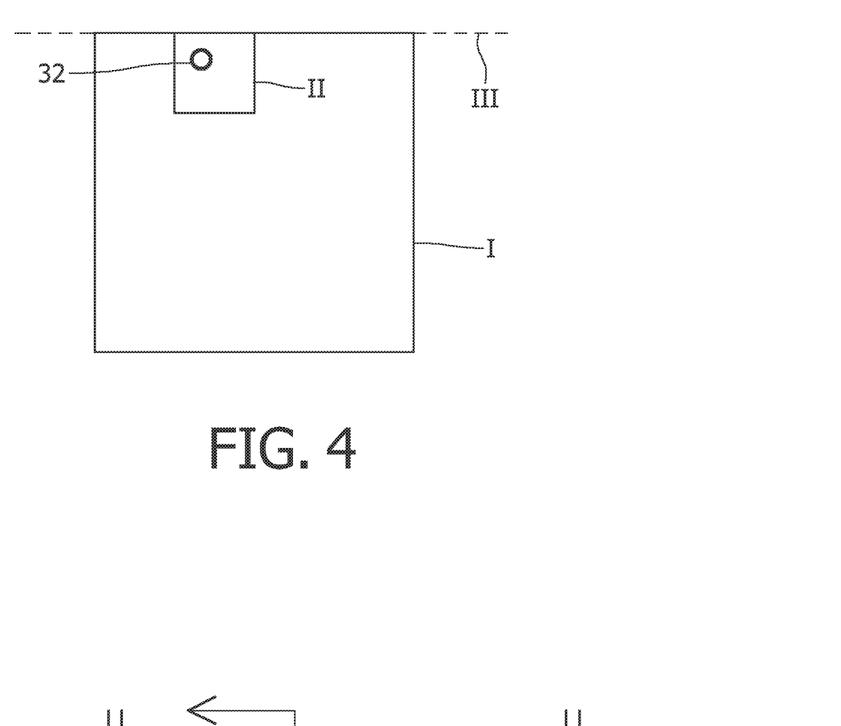
FIG. 4 diagrammatically indicates first and second fields of view, including one hair on skin.

FIG. 4 diagrammatically indicates fields of view of the first and second image sensor, including one hair on skin.

The area indicated by I is a square of about 2×2 mm. It is about $\frac{1}{100}^{th}$ of the surface area of an average field of view of a CCD sensor as suggested by the dashed line III. The area I of 2×2 mm represents the average surface area per hair 32 of a human beard. The hair 32 has been drawn to scale, albeit diagrammatically, having a diameter of about 120 micrometer. Also indicated is a surface area denoted by II. This denotes an average surface area as may be scanned by a present day 3D scanner sensor. Its dimensions are about 0.5×0.5 (×0.5) mm. It is clear from this Figure that a relatively small part of the total field of view of the first (CCD) sensor need be scanned by the second image sensor (surface area II). As the 3D scan of the latter image sensor takes relatively more time, more efficient use can be made of said second image sensor.

Figure 5:
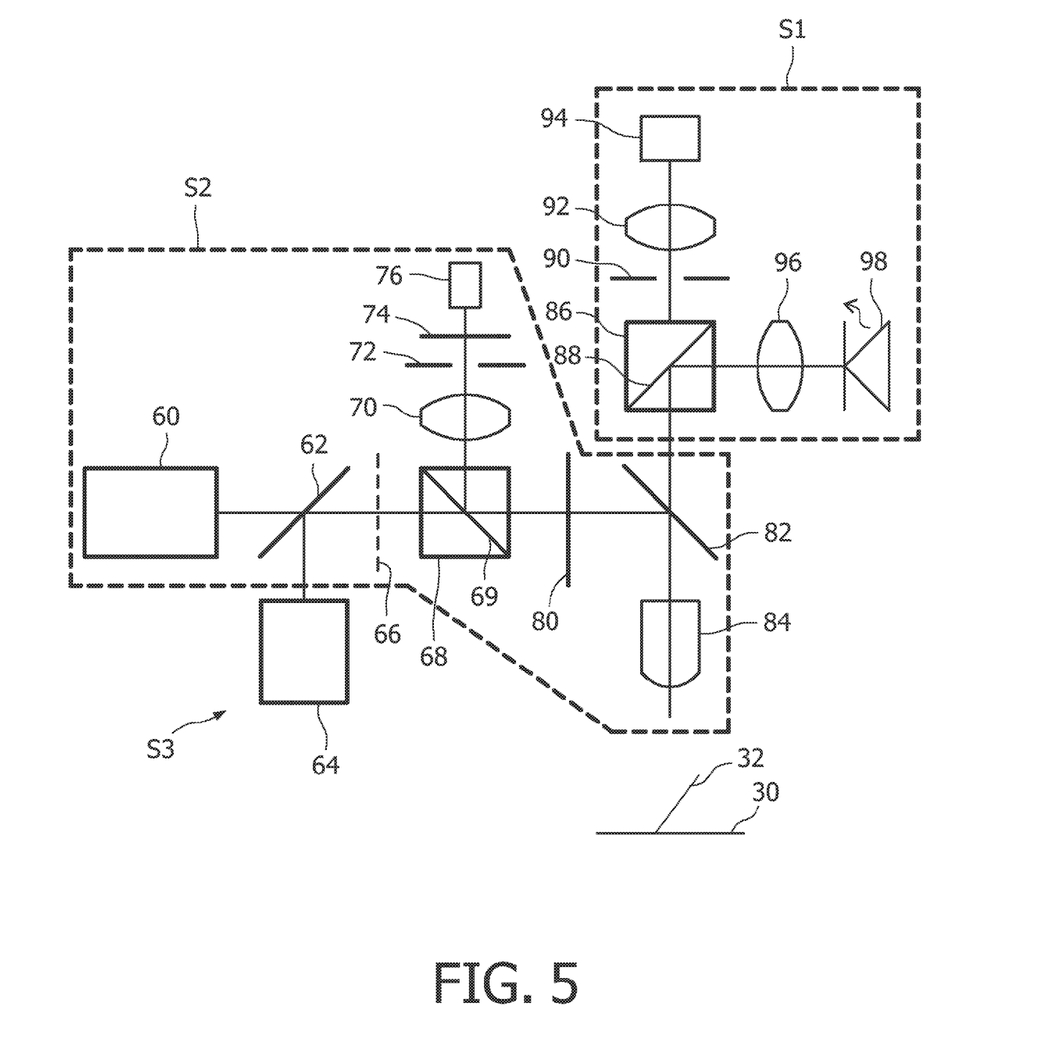
FIG. 5 diagrammatically shows a hairremoval system according to the present invention in more detail.

FIG. 5 diagrammatically shows a hair-removal system according to the present invention in more detail. Herein, S1 generally denotes a first image sensor, S2 denotes a second image sensor and S3 denotes a hair-removal system.

The second image sensor S2 comprises a detection laser 60, a beam splitter 62, a shutter 66, a first polarizing beam splitter 68 with a first beam splitting surface 69, a first lens 70, a first pinhole 72, a bandpass filter 74 and a detector 76. Furthermore, it comprises a λ/4 plate 80, a mirror 82, and an object lens 84.

The first image sensor S1 generally comprises a second polarizing beam splitter 86 with a second beam splitting surface 88, a diaphragm 90, a tube lens 92 and a CCD 94, as well as a LED lens 96, and a LED 98.

The hair-removing device comprises a cutting laser 64. The cutting laser 64, as well as the detection laser 60, the detector 76 and the CCD 94 and the object lens 84 may all be connected to a control unit (not shown). Furthermore, the detection laser 60 and the cutting laser 64 may also be one and the same laser, especially if this is an adjustable laser. Furthermore, various parts are optional, such as, in the latter case, beam splitter 62, shutter 66, polarizing beam splitters 68 and 86, pinholes 72 and 90, λ/4 plate 80 and mirror 82.

In the embodiment shown, light for the CCD detection method of the first image sensor S1 is emitted by the LED 98 with optional LED lens 96. Part of the radiation is reflected by the surface 88, passes the mirror 82 which is transparent to LED radiation but highly reflective to, in this case, e.g., 1064 nm radiation and strikes the skin 30 with a hair 32. An image thereof is reflected and again passes the second polarizing beam splitter 86, the pinhole 90, the tube lens 92, and is detected by the CCD 94. Note that the object lens 84 may be movable, and may be moved out of the way. Note that light or other radiation, such as infrared radiation, may also be supplied directly, i.e. not confocally. For example, a LED might shine directly onto the skin. In such cases, a beam splitter 86 would not be required.

Figure 6A:
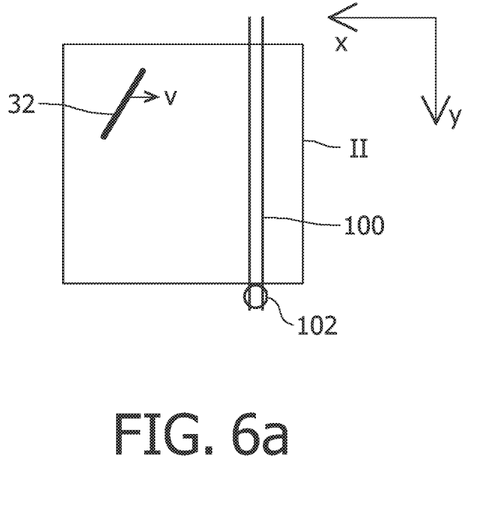
FIGS. 6A and 6B show two steps of a method of determining a hair position and cutting the hair.
Figure 6B:
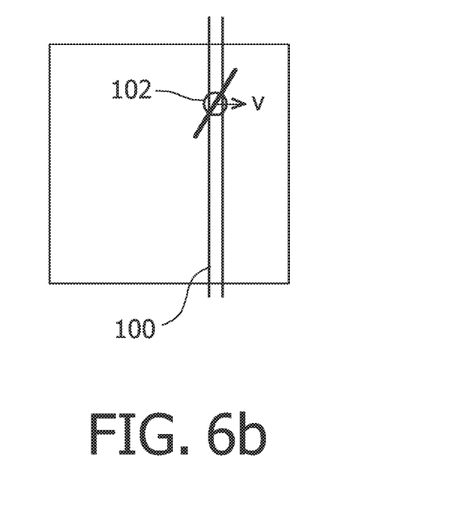

FIGS. 6A and 6B show two steps of a method of determining a hair position and cutting the hair. Herein, II shows an image of a part of the skin, with one hair 32 present. 100 denotes a guiding rail and 102 denotes a movable lens.

In use, the complete system will be moved across the skin. Since movement is relative, this is shown in FIG. 6A as a hair 32 moving with a velocity v in the direction of the arrow as shown. By the use of the first and the second image sensors, the rough position of the hair 32 in x and y is determined. Then, the movable lens 102 is moved along the guiding rail 100 to this x,y position, see FIG. 6B, where the z-position is determined by scanning. Furthermore, as soon as the position in three dimensions has been determined sufficiently accurately, the hair may be removed, by firing a laser, electrical epilating through appropriate positioning of electric needles, etc.

For the above, a numerical example may be as follows. An average velocity v when shaving is about 5 cm/s. A useful resolution in x, y is about 20 micrometer. With a common 1000×1000 pixel camera, this would result in a total field of 2 cm×2 cm. This in turn results in a frame rate of the camera of 2.5 kHz, or an acquisition time of 0.4 ms. This can easily be obtained with a CMOS system. The movable lens 102 may, for example, be the lens of a DVD sled, which has a typical access time of 15 ms (66 Hz). While a DVD actuator unit has a resolution of about 20 nm, only about 20 μm resolution is needed. This less strict demand in respect of resolution may also result in even shorter access times. The actuator for the movable lens can move the lens along the y,z direction over 1-2 mm with 5-6 kHz (0.16-0.20 ms). Once the movable lens is set to the proper position, the actuator, with the lens, can scan locally in a 3D method as explained earlier. In the correct position, again, the hair may be removed with any suitable technique.

A limiting time of the above embodiment is the access time of the movable lens, which is approximately 15 ms. For a typical human beard having about 12.000 hairs, this would result in a shaving time of about 3 minutes, which is a normal time for a shave.

Figure 7:
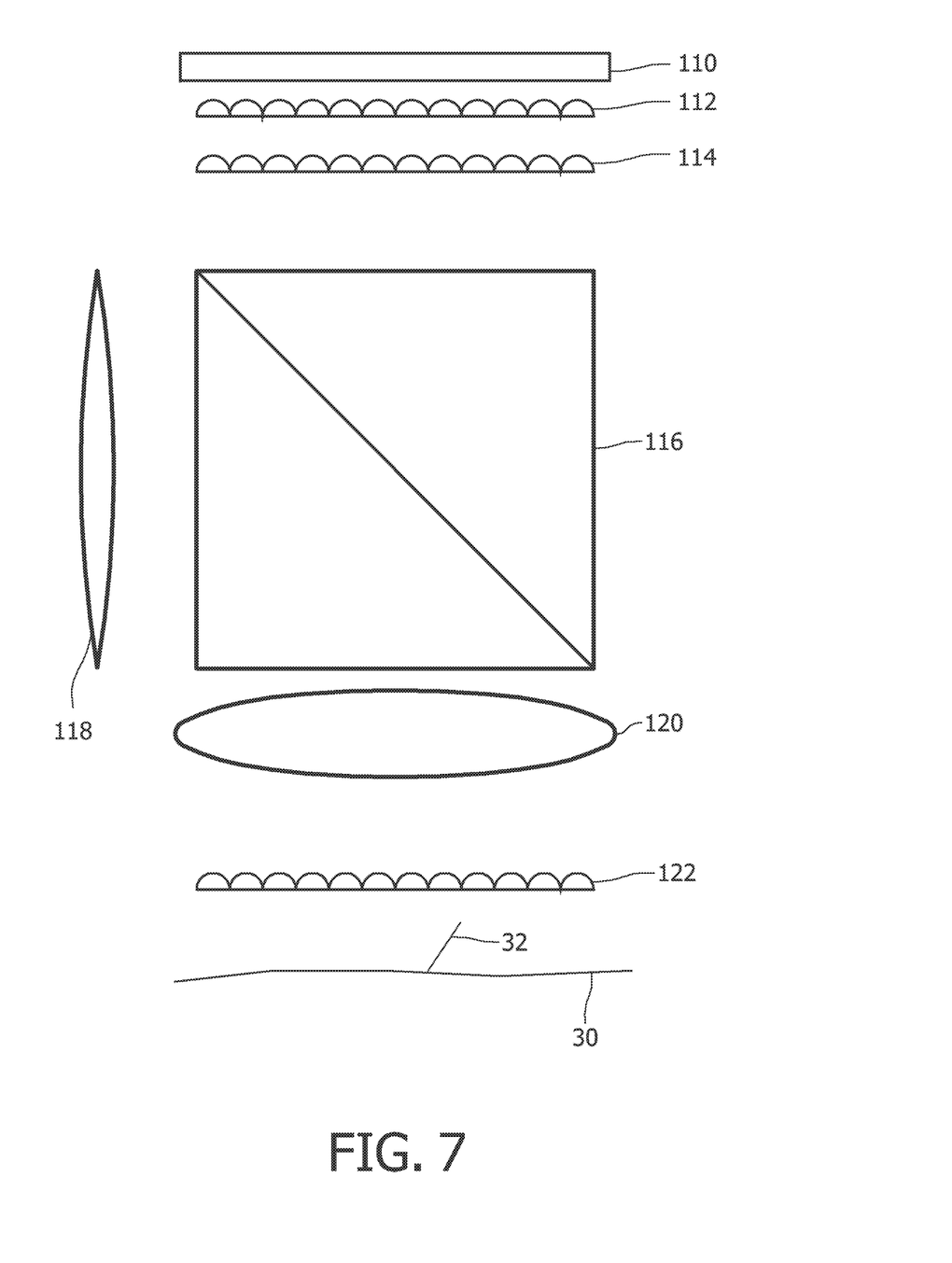
FIG. 7 depicts another embodiment of an image sensor in a system according to the invention.
Figure 8:
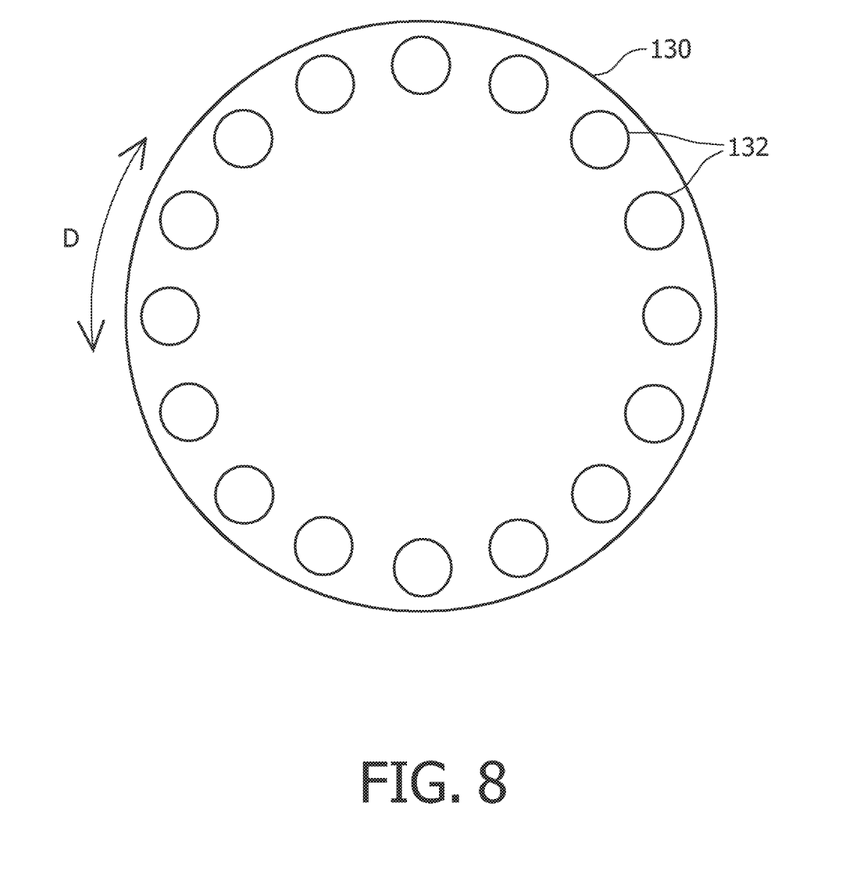
FIG. 8 shows a rotatable array of lenses for another embodiment of an imaging sensor for the system according to the invention.

In another embodiment, that is depicted in FIGS. 7 and 8, use is made of a plurality of lenses, or lens arrays. In particular, 110 is an image sensor (e.g., CCD/CMOS), a first, second and third movable lens array are denoted by 112, 114, and 122, respectively. 116 is a polarizing beam splitter, 118 is a ring light aperture, 120 is a lens. Various other components, such as light sources, a λ/4 plate, a control unit, etc., are not shown here. 30 denotes skin with a hair 32.

In the embodiment of FIG. 7, a first imaging step, the 2D imaging step, is depicted. Herein, the apertures of the third lens array 122 are projected by lens 120 onto the apertures of the second lens array 114, which in turn are projected onto the apertures of the first lens array 112, which in turn are projected on the image sensor 110. Now, the image of the object, in this case skin 30, is projected on the image sensor 110 such that the individual lens images are not each mirrored. Every lens produces a small part of a larger image of the object. At the same time, this lens 120 projects the light-emitting ring light aperture 118 on the third lens array 122.

For the purpose of the present invention, these lens arrays are each subjected to a substantially identical continuous motion in a harmonious fashion, e.g. rotational or vibrational, in the plane of the image sensor 110. At the same time, the whole system is moved laterally over the skin 30 by the user of the system, to perform the shaving action. In all, each lens of the three lens arrays that constitute a single facet of the imaging system generates a projection of the region of interest, or field of view, on the image sensor 110 in a repetitive manner.

For the purpose of the present invention, every point on the object 30, 32, within the field of view of the third lens array 122 is preferably, but not exclusively, imaged with such a frequency that the lateral displacement from scan to scan due to the user's lateral motion is roughly equivalent to, and not much more than, the intended lateral target resolution of, say, 20 μm.

The sensor 110 is undergoing the same lateral displacement as the lens arrays, but not the harmonic motion. As a consequence, the image of the object 30, 32, as projected on the sensor 110, moves at the same lateral speed as the lenses of the lens arrays and image sensor combination, while the harmonic (rotating, vibrating, . . . ) motion is only experienced by the lens arrays 112, 114, 122.

In the embodiment shown, the lens 120 serves to project the apertures of the third lens array 122 onto those of the second lens array 114. Hereby, a considerable amount of space is made available on either side of the lens 120, which space can be used for the second stage of the detection process, to be discussed later, and for coupling in light that is needed for the image formation.

For this latter purpose, use is made in this case of the polarizing beam splitter 116. The light emitted by the ring light aperture 118, and supplied by, e.g., fiber optics, a (halogen) incandescent lamp, one or more LEDs, and the like, is projected by means of the additional lens 120 on the apertures of the third lens array 122 in such a way that each lens in that array illuminates its respective field of view in a more or less homogeneous fashion. In practice, this may be achieved by imaging the light from the ring light aperture 118 in the back focal plane of the lenses in the third array 122. This is done preferably by ensuring that a light distribution as emanating from the aperture 118 occurs in a similar fashion as the distribution of the plurality of lenses. This will be further elucidated with reference to FIG. 8, which shows an array of lenses.

In a numerical example to show the feasibility, it is assumed that the required resolution is 20 μm, although of course other values may also be taken. The speed at which the user moves the system over the skin is taken to be at most 5 cm/s. Again, for other cases, these values may be adapted, causing corresponding changes to the following figures.

Assume furthermore that the lens arrays consist of a disc of about 2 cm diameter with a number of 2 mm aperture lenses regularly spaced around the circumference, see FIG. 8. Although 16 lenses are shown, it is assumed in this numerical example that 25 lenses are present. In order to scan the entire ring image once, the ring of lenses needs to turn 360/25=14.4 degrees, indicated by arrow D. Hence, in order to achieve the desired resolution of 20 μm in the entire field, while the device is being moved at 5 cm/s, the disc needs to rotate at a rate of about 100 Hz, such that the area is imaged every 0.020/50 s=400 μs, or at a refresh rate of 2.5 kHz. The 2D image is recorded by means of the image sensor 110, such as a CCD or CMOS imaging sensor, preferably at the same refresh rate (2.5 kHz) so that only very minor motional blurring will occur. Furthermore, to ensure that a surface area of 2×2 cm will be imaged with a resolution of 20 μm, at least 1000×1000 pixels are required. Both this number and the required refresh rate are easily achievable with today's CCD and CMOS technology. It will be clear that other shapes of and values for the disc, number and aperture of lenses et cetera, are possible, which will require an adaptation of the other figures.

The above imaging is a first step in the total imaging process according to the invention, in which a 2D image is obtained. Note that a resolution of 20 μm or similar is not yet required at this stage. A lower resolution may be selected, with a reduced acquisition time, as long as an approximate target position can be obtained. A more exact position, with the desired resolution, may be obtained in the second stage of the imaging, i.e. with the second image sensor.

In the second imaging step, the presence of a specific target, such as a hair, is either detected at a specific and fixed depth (or z-position), or scanned in order to determine its position and orientation in space. These options may be selected for every method, and corresponding device, of the invention. In the example described here, the first option is selected, e.g., in order to shave hairs off at a certain length. The presence of the target at the specified depth is determined, e.g., by means of cross-polarized confocal laser scanning. For this purpose, a laser beam is aimed through a selected lens of the third lens array 122. This selected lens will focus the laser beam in a point that is moving parallel to the moving lens, i.e. rotating, vibrating and the like. The lens will collimate light that is reflected back from the focal volume. When such a first, selected lens is moving completely out of the laser beam, a second, neighboring lens will enter the laser beam and perform a new scan. Thus, the lateral resolution of the detection is dictated by the resolution of the confocal scan, and the distance between consecutive scans is determined by the speed at which the system as a whole moves over the target area of the skin. The intensity of the reflection of the orthogonally polarized light that is reflected or scattered back from the target area is confocally detected by means of the polarizing beam splitter 116 and a lens-pinhole combination, not shown here, but cf FIG. 5. The amount of light captured by the detector, as well as its variation as a function of the lens position and thus as a function of time, may provide information on the presence of various structures in the focal area (field of view) and thereby ascertain the 3D position and/or orientation thereof.

Embodied as a laser shaver, the system could function as follows. The first imaging sensor detects an image of skin with hair, and the control unit, not shown but either on-chip (CMOS) or as a separate module, determines an approximate position of the hair(s) on the skin. The accuracy may, e.g., be about 100 or 200 μm. Once this coarse position has been established, the control unit can aim a detection laser, e.g., by means of a deflection unit (not shown but cf. 52, 54 of FIG. 3), such as a MOEMS (micro-optical-electrical mechanical system) or other type of movable mirror, and a dichroic mirror between the third rotating lens array 122 and the lens 120, towards the position on the rotating lens array where the hair was approximately found.

Next, the control unit records the results from the confocal laser scan, and interprets the results, i.e. the second imaging step. Once the presence and position of the hair has been established by the cross-polarized 3D detection method, and it has been determined that the position of the hair relative to the lens focus is within the desired accuracy, the detection system enables the cutting laser, which emits continuous or pulsed laser radiation that is coupled into the lens collinearly or at a known angle and thus is focused at the original detection laser focus spot or at a known distance from that focus, respectively. The radiation from the cutting laser then cuts the hair.

Various aspects of the methods and devices as described above, without explicitly mentioning them here, may be employed or varied by the skilled person. For example, it will be clear that it is advantageous if the detection laser beam passes only one lens of the lens array(s) at a time; in other words, the laser beam diameter is preferably smaller than the lens pitch to avoid ambiguous detection results. Furthermore, the shape of the disk 130, the number, pitch and size of the lenses 132, their motion etc., may all be varied in the method, as long as required corresponding quantities etc., are also adapted. Even more explicitly, the above-described example only serves to show the applicability of the proposed invention. Furthermore, in all of the above, a preferred method of removing hairs was cutting them with a laser beam. However, other ways of removing them are also possible in the context of the invention, such as electrical epilation, or only damaging the hairs or roots thereof, etc. In all cases, knowing the exact position, and sometimes also the orientation, of individual hairs is required to remove the hairs. Finding that position in particular in three dimensions may take a lot of time. The invention provides a system and method to reduce that time by providing a rough pre-imaging step and a second imaging step to find the three dimensions of the position with the required precision. The final 3D position may be found by taking the first two coordinates of the first imaging step, and adding a third coordinate in the second imaging step, or all three coordinates may be determined in the second step, after a first rough estimate in the first 2D step, etcetera.

The invention has been described and elucidated with respect to exemplary embodiments and Figures. The scope of the invention may be determined by the appended claims.

The invention claimed is:

1. A hair-removing system comprising:
a first image sensor configured to scan skin in at least a first scanning direction and detect a two-dimensional image of the skin to be treated;
a second image sensor configured to scan a part of the skin in at least a second scanning direction making a non-zero angle with the image and provide hair position information;
a control unit coupled to the first and second image sensors configured to discern in the image of the skin, the part of the skin having the hair and the hair position information; and
a hair-removing device operatively coupled to the control unit and the first image sensor.

2. The hair-removing system according to claim 1, wherein the second image sensor is able to provide a higher spatial information density than the first image sensor, in their respective image.

3. The hair-removing system according to claim 1, wherein the first image sensor comprises: one of a 2D optical image sensor, a charge coupled device, a CMOS device, and a focal plane array of photodetectors.

4. The hair-removing system according to claim 1, wherein the first image sensor is constructed to detect an image of a part of the skin of at least 1 cm×1 cm.

5. The hair-removing system according to claim 1, wherein at least a part of the second image sensor is movable with respect to the first image sensor.

6. The hair-removing system according to claim 1, wherein the second image sensor has, in at least one dimension, a higher resolution than a resolution of the first image sensor in that dimension.

7. The hair-removing system according to claim 1, wherein the second image sensor is constructed to scan a selected part of the part of the skin to be treated, to thus provide an image thereof, in a third dimension outside the two-dimensional image of the first image sensor.

8. The hair-removing system according to claim 1, wherein the second image sensor comprises a 3D image sensor and an adjustable lens that is adjustable separate from the 3D image sensor and is movable in a direction perpendicular to the part of the skin to be treated.

9. The hair-removing system according to claim 8, wherein the lens is movable in a direction that is substantially parallel to the part of the skin to be treated.

10. The hair-removing system according to claim 1, further comprising a light source.

11. The hair-removing system according to claim 10, wherein the light source comprises a LED or a laser source.

12. The hair-removing system according to claim 11, wherein the laser source is adjustable.

13. The hair-removing system according to claim 12, wherein the laser source is adjustable between a first power level that enables detection without damage to the skin and/or hair, and a second power level that enables inflicting sufficient energy to the hair for the hair to be subsequently removed.

14. The hair-removing system according to claim 12, further comprising a controller for adjusting a laser source beam width.

15. A method of detecting and removing a hair on skin, the method comprising:
    scanning in at least a first scanning direction a substantially two-dimensional image of a first part of a skin to be treated by a first image sensor,
    selecting, by a control unit and a second image sensor, a second portion of the part of the skin selected from the first part of the skin, the two-dimensional image of which is selected to contain at least one hair,
    scanning the selected second portion with the second image sensor in at least a second scanning direction that makes a non-zero angle with the image, in order to obtain a position and/or orientation of the hair in three dimensions,
    operating the hair-removing device to remove the hair.

* * * * *